(12) United States Patent
Null et al.

(10) Patent No.: US 7,011,665 B2
(45) Date of Patent: Mar. 14, 2006

(54) GUIDE ASSEMBLY FOR ENGAGING A BONE PLATE TO A BONY SEGMENT

(75) Inventors: William B. Null, Olive Branch, MS (US); Brian A. Burd, Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 319 days.

(21) Appl. No.: 10/200,397

(22) Filed: Jul. 22, 2002

(65) Prior Publication Data
US 2004/0015174 A1    Jan. 22, 2004

(51) Int. Cl.
*A61B 17/58* (2006.01)
(52) U.S. Cl. ........................................................ 606/99
(58) Field of Classification Search .................. 606/86, 606/96, 104, 105, 91, 99, 69, 70, 71
See application file for complete search history.

(56) References Cited

U.S. PATENT DOCUMENTS

| | | | | |
|---|---|---|---|---|
| 1,831,813 | A | * | 11/1931 | Levedahl ..................... 408/81 |
| 4,383,527 | A | * | 5/1983 | Asnis et al. .................. 606/96 |
| 4,744,353 | A | * | 5/1988 | McFarland .................. 606/96 |
| 5,423,826 | A | | 6/1995 | Coates et al. |
| 5,669,915 | A | | 9/1997 | Caspar et al. |
| 5,676,666 | A | | 10/1997 | Oxland et al. |
| 5,755,721 | A | | 5/1998 | Hearn |
| 5,851,207 | A | | 12/1998 | Cesarone |
| 6,066,142 | A | | 5/2000 | Serbousek et al. |
| 6,193,721 | B1 | | 2/2001 | Michelson |
| 6,235,034 | B1 | | 5/2001 | Bray |
| 6,332,887 | B1 | | 12/2001 | Knox |
| 6,342,056 | B1 | | 1/2002 | Mac-Thiong et al. |
| 6,342,057 | B1 | | 1/2002 | Brace et al. |
| 6,379,364 | B1 | | 4/2002 | Brace et al. |
| 6,416,518 | B1 | | 7/2002 | DeMayo |
| 6,436,103 | B1 | | 8/2002 | Suddaby |
| 6,592,586 | B1 | * | 7/2003 | Michelson ................... 606/71 |
| 6,692,503 | B1 | * | 2/2004 | Foley et al. .................. 606/96 |
| 2001/0047172 | A1 | | 11/2001 | Foley et al. |

FOREIGN PATENT DOCUMENTS

EP    0 460 447 A1    5/1991

OTHER PUBLICATIONS

Thomas A. Zdeblick, M.D. and Harry N. Herkowitz, M.D.; Premier Anterior Cervical Plate System, Surgical Technique; Premier Anterior Cervical Plate System; 2000 Medtronic Sofamor Danek.

ZEPHIR Anterior Cervical Plate System, Surgical Technique; 2000 Medtronic Sofamor Danek; pp 1-8.

Gary L. Lowery, MD, PhD; Sugical Technique; ORION Anterior Cervical Plate System; Sofamor Danek The Spine Specialist; pp 1-24.

* cited by examiner

*Primary Examiner*—Eduardo C. Robert
(74) *Attorney, Agent, or Firm*—Krieg DeVault LLP (57) ABSTRACT

A surgical instrument guide assembly is positionable on a bone plate. The instrument guide assembly includes at least one guide member alignable with a corresponding fastener opening in the bone plate when the guide assembly is positioned on the bone plate. The at least one guide member can guide various surgical instruments through the fastener hole in the plate.

20 Claims, 6 Drawing Sheets

GUIDE ASSEMBLY FOR ENGAGING A BONE PLATE TO A BONY SEGMENT

BACKGROUND

The use of bone plates for a variety of orthopedic applications is widely practiced. The plates are used to align, mend, and/or alter adjacent bony segments in a patient using a plurality of fasteners such as screws installed through openings in the plate. Correct orientation and alignment of fasteners can be important to proper engagement and positioning of the bone plate relative to the bony segment to which it is engaged.

Bone plates used in spinal applications can be particularly sensitive to positioning and engagement to bony segments of the spinal column. Spinal bone plates can be used for long term, intravertebral and intervertebral fixation and stabilization. Because of the spinal cord and other sensitive anatomical structures adjacent the spinal column, and the relatively small size of the vertebral areas, the desired areas of positioning and alignment of bone engaging fasteners to secure the bone plate to the particular bony segment of the spinal column can be relatively small. A guide assembly capable of maintaining alignment of surgical instruments with respect to a bone plate during engagement of the bone plate to a bony segment is desired.

SUMMARY

The present invention relates to a guide assembly positionable relative to bone plate to provide an alignment therebetween for the positioning and engagement of bone engaging fasteners through holes in the bone plate.

According to one aspect of the invention, there is provided a guide assembly for a bone plate. The guide assembly includes at least one guide member alignable with a fastener hole of the bone plate and a handle extending proximally from the guide member. A base is adapted to support the guide member on the bone plate. The base has a foot member engageable with the bone plate and a biasing member contactable with the bone plate to bias the base proximally from the bone plate.

According to another aspect of the invention, there is provided a guide assembly for a bone plate. The guide assembly includes at least one guide member and a handle extending proximally from the at least one guide member. A base positionable relative to the bone plate supports the at least one guide member in alignment with a fastener hole of the bone plate. The base includes a first member contactable with a distal surface of the bone plate and a second member contactable with one of a proximal surface of the bone plate and bony structure underlying the bone plate to secure the at least one guide member in alignment with the fastener hole of the plate.

According to a further aspect of the invention, there is provided a system that includes a bone plate and a guide assembly. The bone plate includes a receptacle and at least one hole for a bone engaging fastener. The guide assembly includes a handle and a guide member extending from the handle that is alignable with the at least one hole of the bone plate. The guide assembly also includes a base extending from the guide member. The base includes a first member positioned in the receptacle and a second member distally biased toward the bone plate.

According to another aspect of the invention, a system is provided that includes a bone plate and a guide assembly. The bone plate includes a receptacle and at least one hole for a bone engaging fastener. The guide assembly includes a handle and a guide member extending from the handle alignable with the at least one hole. The guide member includes a distal end spaced from a proximal surface of the bone plate. The guide assembly further includes a base positionable in the receptacle. The base includes a member in contact with the bone plate that has a variable length so that the guide member can assume any one of a plurality of positions relative to the bone plate.

According to a further aspect of the invention, a guide assembly for a bone plate is provided. The guide assembly includes at least one guide member alignable with a fastener hole of the plate and a handle extending from the at least one guide member. The guide assembly further includes means for supporting the at least one guide member relative to the bone plate with the at least one guide member aligned with the fastener hole. The means for supporting includes means for biasing the means for supporting proximally relative to the plate.

According to another aspect of the invention, there is provided a method for positioning a guide assembly relative to a bone plate having at least one fastener hole and a receptacle. The method includes sliding a foot member of guide assembly into a receptacle in the bone plate; and biasing the guide assembly proximally relative the bone plate to secure the foot member in the receptacle.

These and other aspects of the invention will also be provided in the following description.

DETAILED DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and modifications in the illustrated devices and methods, and any further applications of the principles of the invention as illustrated herein, are contemplated as would normally occur to one skilled in the art to which the invention relates.

Figure 1:
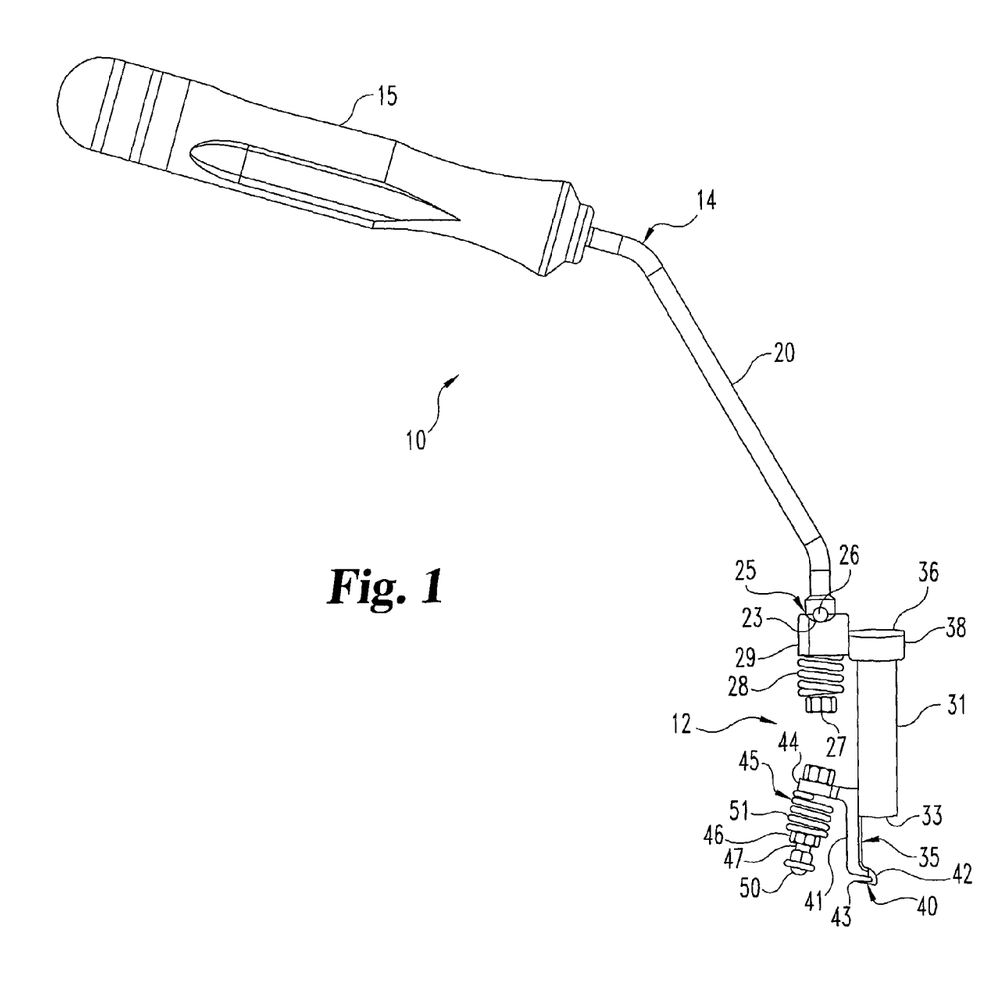
FIG. 1 is a side view of a guide assembly for guiding instruments to secure a bone plate to a bony segment according to the invention.
Figure 2:
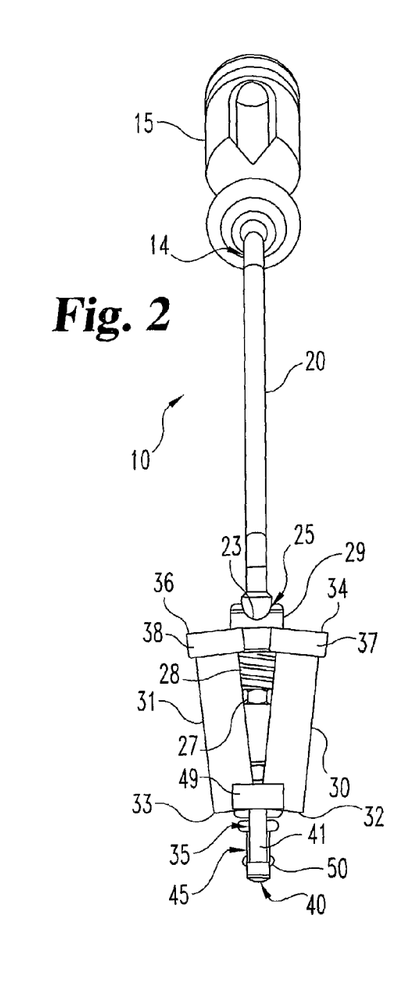
FIG. 2 is a front view of the guide assembly of FIG. 1.

Referring to FIGS. 1 and 2, there is shown one embodiment of a guide assembly adapted for use with a bone plate having one or more fastener openings. Guide assembly 10 includes one or more guide members alignable with fastener openings of the bone plate to guide drilling, tapping, and/or fastener placement through the aligned fastener hole of the plate.

Guide assembly 10 includes a handle assembly 14 including a handle 15 and a shaft 20 extending distally from handle 15. A distal guide portion 12 extends distally from shaft 20. In one embodiment, handle assembly 14 can be rotated relative to guide portion 12 about a coupling assembly 25. In another embodiment, handle assembly 14 can be fixed and/or non-rotatable relative to guide portion 12.

In the illustrated embodiment of the rotatable handle assembly 14, shaft 20 includes distal pin 27 extending through and rotatably received in a central passage extending through a coupling member 29. A spring 28 extends between coupling member 29 and a head of pin 27 to bias shaft 20 distally into contact with coupling member 29. To fix shaft 20 relative to coupling member 29, shaft 20 includes a locking member 26 extending laterally therefrom received in certain ones of notches 23 positioned about a proximal end of coupling member 29.

In the illustrated embodiment, locking member 26 is received in notches 23 so that handle 15 extends away from guide portion 12. Handle assembly 14 could be repositioned relative to guide portion 12 by lifting handle 15 to compress biasing member 28 between coupling member 29 and the head of pin 27 sufficiently to remove locking member 26 from notches 23. Shaft 20 can be rotated 90 degrees in either direction in coupling member 29 to reposition locking member 26 in another notch, such as the notch 23 shown in FIG. 2, where handle 15 would extend laterally from guide portion 12. It is also contemplated that shaft 20 include a second locking member extending therefrom opposite the illustrated locking member 26 to position the second locking member in the opposite notch and provide solid engagement between handle assembly 14 and guide portion 12.

It is contemplated that four notches 23 could be provided and spaced at 90 degree intervals about coupling member 29. Other embodiments contemplate additional notches 23 at other locations to provide other orientations between handle assembly 14 and guide portion 12. Handle assembly 14 could also be rotated so that shaft 20 and handle 15 extend across guide portion 25.

Coupling assembly 25 further includes a pair of guide member receiving portions 37, 38 extending from coupling member 29. Guide member receiving portions 37, 38 can each include a ring-like configuration with a passage sized to receive respective ones of the guide members 30, 31 of guide portion 12 therethrough. In one embodiment, guide members 30, 31 can be guide tubes each having a passage extending therethrough and opening at, for example, a proximal end 34 and a distal end 32 of guide member 30 and at a proximal end 36 and a distal end 33 of guide member 31. Other arrangements for guide members 30, 31 are also contemplated that are suitable for guiding instruments in alignment with a fastener hole of a bone plate upon which guide assembly 10 is positioned. It is further contemplated that guide assembly 10 could be provided with a single guide member, or with more than two guide members.

In order to support guide assembly 10 on a bone plate, there is provided a base 35 that is positionable with respect to a bone plate to secure guide assembly 10 thereto with guide members 30, 31 in alignment with respective fasteners holes of the bone plate. Base 35 includes a first member 40 and a second member 45 contactable with one or both of the plate and the bony structure underlying the plate to secure guide assembly 10 to the plate.

In one embodiment, base 35 includes a support member 41 extending between a distal end and a proximal end thereof. First member 40 is positioned at the distal end of support member 41 and an extension 44 is positioned at a proximal end of support member 41. Base 35 further includes a guide member engagement portion 49 extending from the proximal end thereof opposite extension 44. Guide member engagement portion 49 can be engaged to guide members 30, 31 to secure guide members 30, 31 and handle assembly 14 to base 35. In the illustrated embodiment, guide member engagement portion 49 extends between guide members 30, 31 and at least partially therearound. Guide members 30, 31 can be engaged to engagement portion 49 by welding, bolting, riveting, screwing, adhering or otherwise attaching guide members 30, 31 thereto.

In the illustrated embodiment, first member 40 is a foot member extending laterally from support member 41, and includes an upper portion 42 and a lower portion 43 defining a space therebetween. Upper portion 42 extends transversely to support member 41 in a first direction, and lower portion 43 extends from an end of upper portion 42 back toward support member 41. Thus, in the illustrated embodiment, the foot member forms a hook-like shape that, as discussed further below, is positionable in a receptacle of the bone plate. Other embodiments contemplate other arrangements for first member 40, such as a threaded shaft or pin, a radially expandable collet, or a configuration that grasps the sides of the bone plate, for example.

In the illustrated embodiment, second member 45 includes a pin 47 movably received in a passage through extension 44. A spring 51 extends between extension 44 and a plate 46 extending about and fixed to pin 47. As indicated by arrows 102, (FIGS. 9 and 10), spring 51 biases a distal end 50 of pin 47 distally, yet allows pin 47 to move proximally relative to extension 44 in response to a force applied proximally to distal end 50. Other embodiments contemplate other arrangements for second member 45, such as a threaded shaft or pin, a radially expandable collet, or a configuration that grasps the sides of the bone plate, for example.

Figure 4:
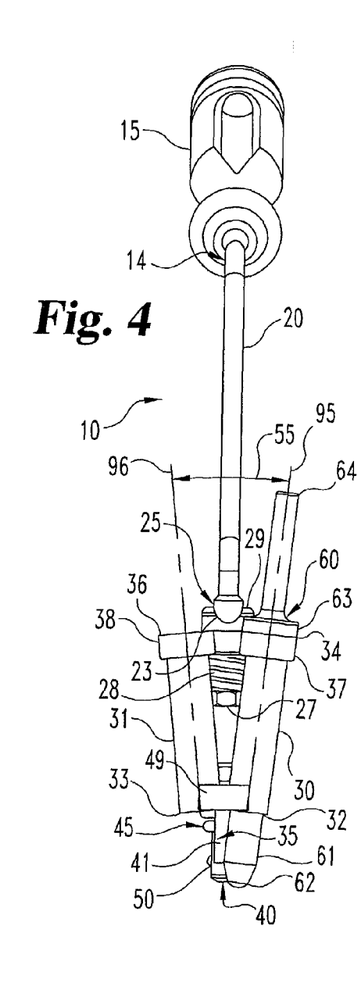
FIG. 4 is a front view of the guide assembly and drill guide of FIG. 3.

With reference to FIGS. 2 and 4, one contemplated arrangement for guide assembly 10 includes a pair of guide members 30, 31. Guide members 30, 31 can be arranged at an angle relative to one another such that distal ends 32, 33 of the guide members 30, 31 are closer to one another than proximal ends 34, 36. Guide members 30, 31 can be centered along longitudinal axes 95 and 96, respectively, such that the axes 95 and 96 converge distally. In one embodiment longitudinal axes 95, 96 converge at an angle 55 of about 12°. Other embodiments contemplate other convergence angles 55 for longitudinal axes 95 and 96 ranging from 1 degree or less to about 45 degrees or more. It is also contemplates that axes 95, 96 could be parallel to one another, or could diverge from one another distally toward the bone plate.

Figure 3:
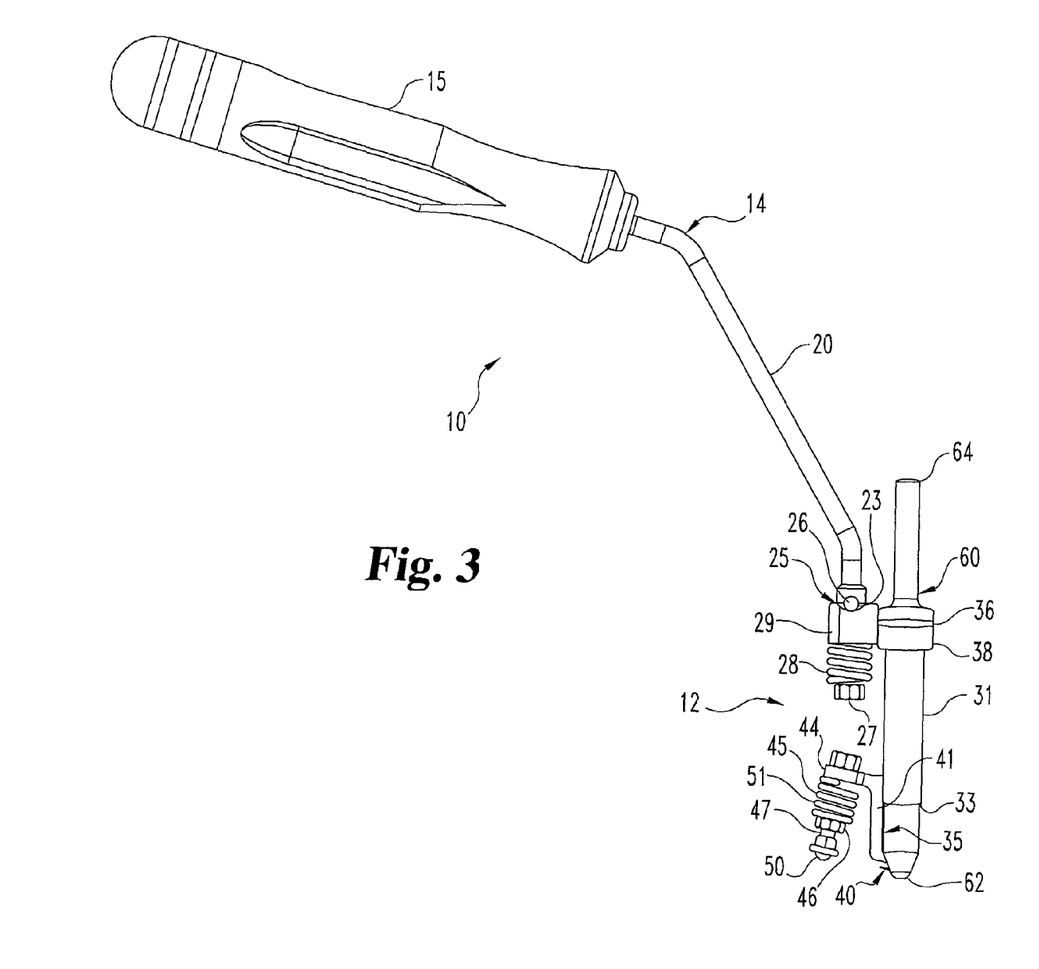
FIG. 3 is a side view of the guide assembly of FIG. 1 with a drill guide.

As shown in FIGS. 3 and 4, guide members 30, 31 can be adapted to guide an instrument guide or a surgical instrument therealong. In this particular example, an instrument guide 60 can be inserted through guide member 30. Instrument guide 60 includes a distal end 62 positioned distally of distal end 32 of guide member 30, and a proximal handle portion 64 that extends proximally of proximal end 34.

Instrument guide 60 can include a main body 61 removably received in form fitting engagement with guide member 30 so that guide member 30 aligns instrument guide 60 along its longitudinal axis 95. A collar 63 can extend radially about main body 61 and handle portion 64 to abut the proximal end of guide member 30 and/or guide member receiving portion 37.

A drill bit, for example, can be inserted in instrument guide 60 to form a hole in the bony structure underlying the plate upon which guide assembly 10 is positioned. It is also contemplated that guide members 30, 31 may accept and align guides for other types of instruments, including tapping instruments and fastener driving instruments. It is further contemplated that such drilling, tapping and fastener driving instruments could be configured for placement and guidance directly through guide members 30, 31.

Figure 5:
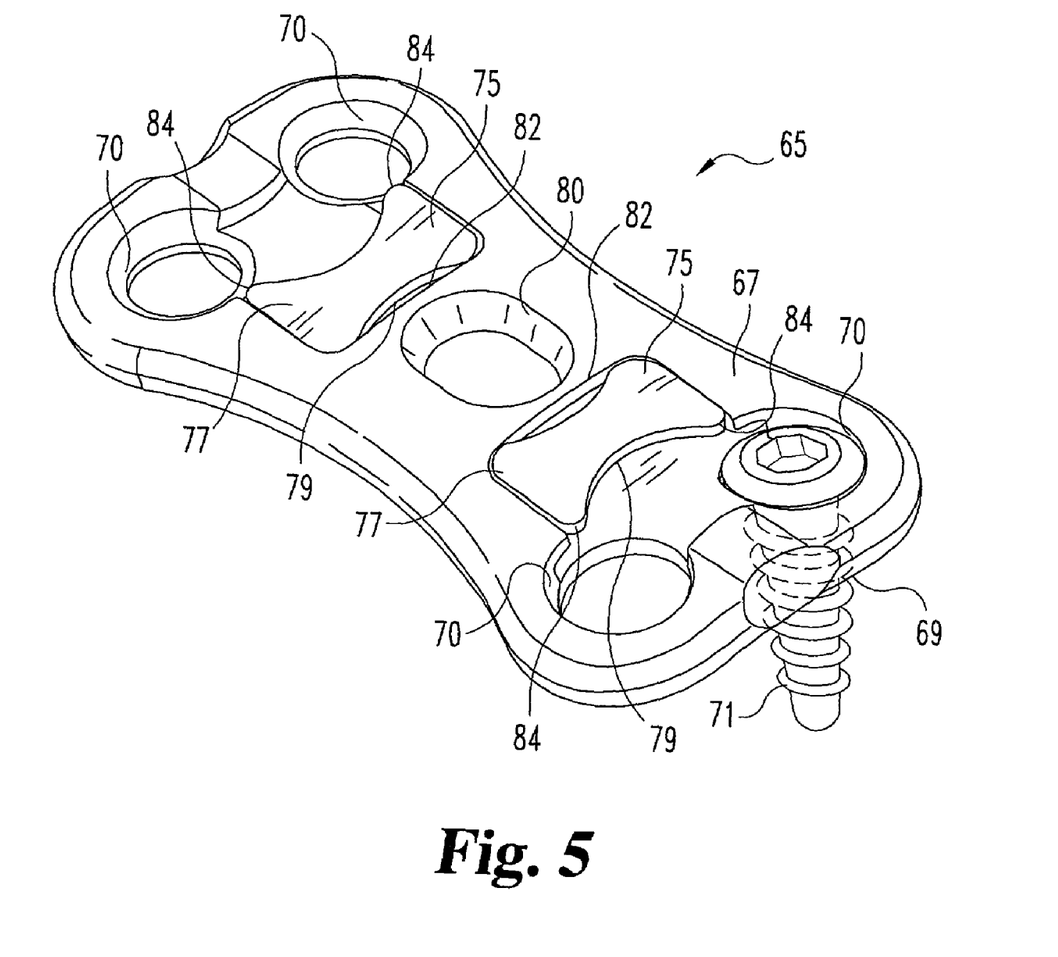
FIG. 5 is a perspective view of one embodiment of a bone plate having application with the guide assembly of FIG. 1.

In one embodiment, guide assembly 10 is adapted for engagement with a bone plate 65 as shown in FIG. 5. Bone plate 65 is one, non-limiting example of a type of bone plate suitable for use with the present invention. Other suitable bone plates may also be used. Bone plate 65 includes a proximal face 67 and a distal face 69, can be provided with a number of fastener openings 70 extending therebetween. A central aperture 80 can also provided in bone plate 65. Bone plate 65 can also include recesses 82 formed in proximal surface 67 in communication with respective pairs of the fastener holes 70. Each of the recesses 82 can be provided with a retaining element 75 slidably captured therein. Retaining members 75 each include a proximal face 77 and a distal face 79. After bone engaging fasteners, such as bone screw 71, are positioned in respective ones of holes 70, each retaining element 75 is movable in its recess 82 so that protrusions 84 contact or extend over at least a portion of respective ones of the heads of the bone engaging fasteners to prevent the bone engaging fasteners from backing out relative to plate 65.

Figure 6:
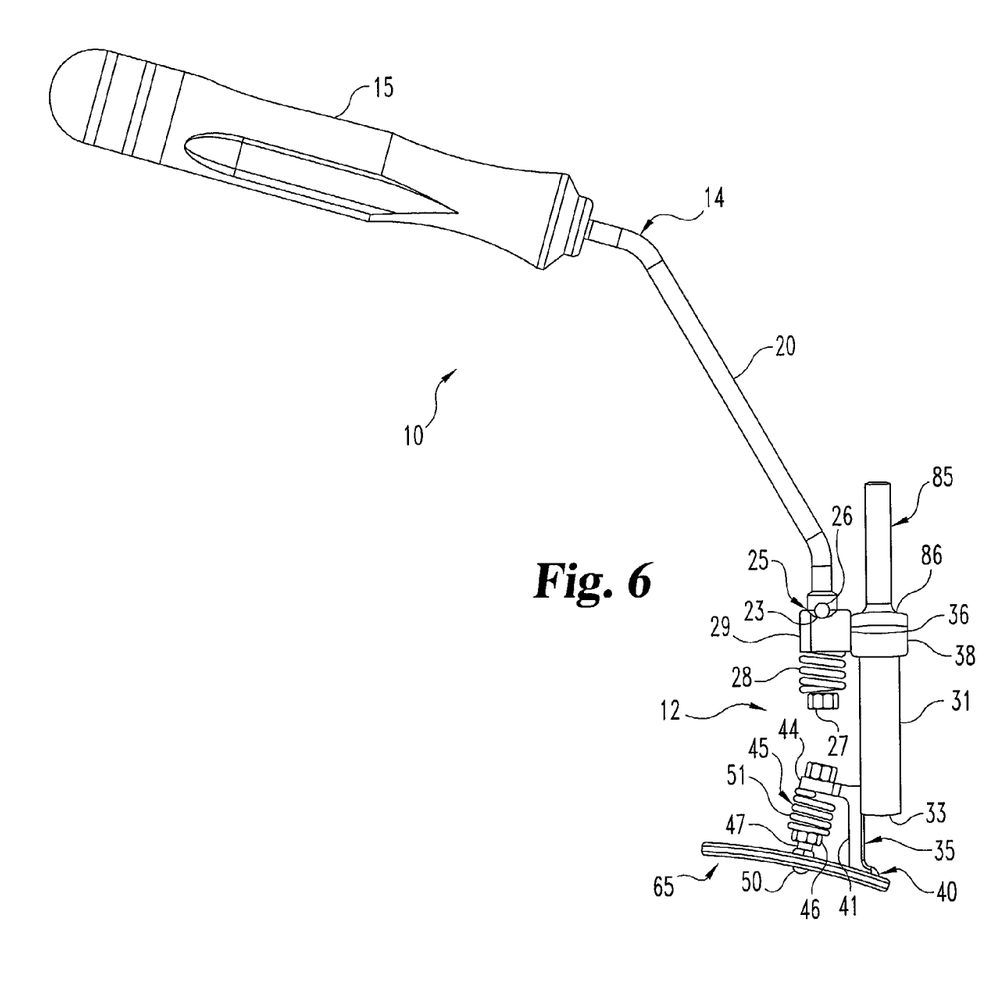
FIG. 6 is a side view of the guide assembly of FIG. 1 positioned on the bone plate of FIG. 5.
Figure 7:
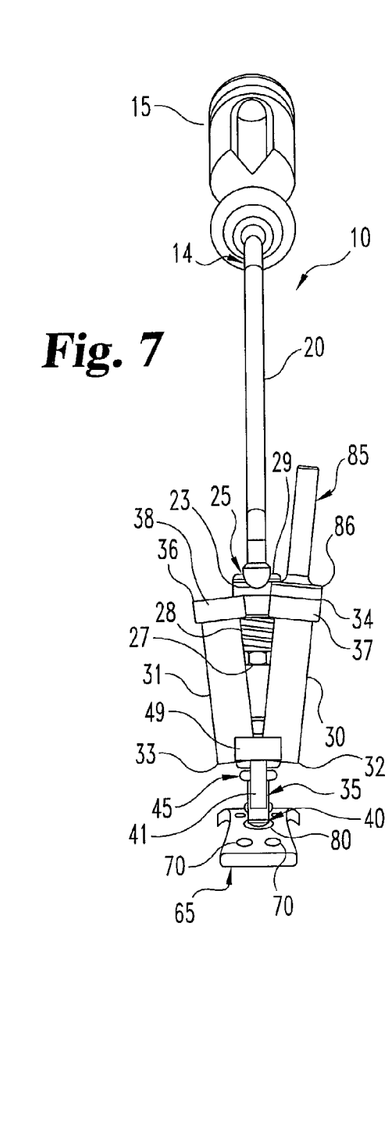
FIG. 7 is a front view of the guide assembly and bone plate of FIG. 5 with one embodiment of a guide positioned in the guide assembly.

FIGS. 6 and 7 illustrate guide assembly 10 positioned on bone plate 65. Base 35 of guide assembly 10 engages bone plate 65 with first member 40 and second member 45. When guide assembly 10 is positioned on bone plate 65, the distal ends 32, 33 of guide members 30, 31 are spaced a distance from proximal surface 67 of bone plate 65 so as to not obstruct the adjacent fastener hole 70. This prevents guide members 30, 31 from obstructing the surgeon's view of the fastener openings of the bone plate, and allows for better visualization of drilling, tapping and/or bone fastener insertion through the plate holes. It also allows bone engaging fasteners to be inserted into the plate holes using guide members 30, 31 since the guide members 30, 31 do not occupy the fastener holes. Other embodiments contemplate guide members 30, 31 which interface with the plate holes.

As shown FIG. 7, another embodiment instrument guide 85 is positioned in and supported on guide member 30. Instrument guide 85 does not engage the bone plate 65 when used but rather is supported by its collar 86 on the proximal end of guide member 30 and/or guide member receiving portion 37 such that its distal end is spaced from proximal surface 67 of bone plate 70.

Figure 8:
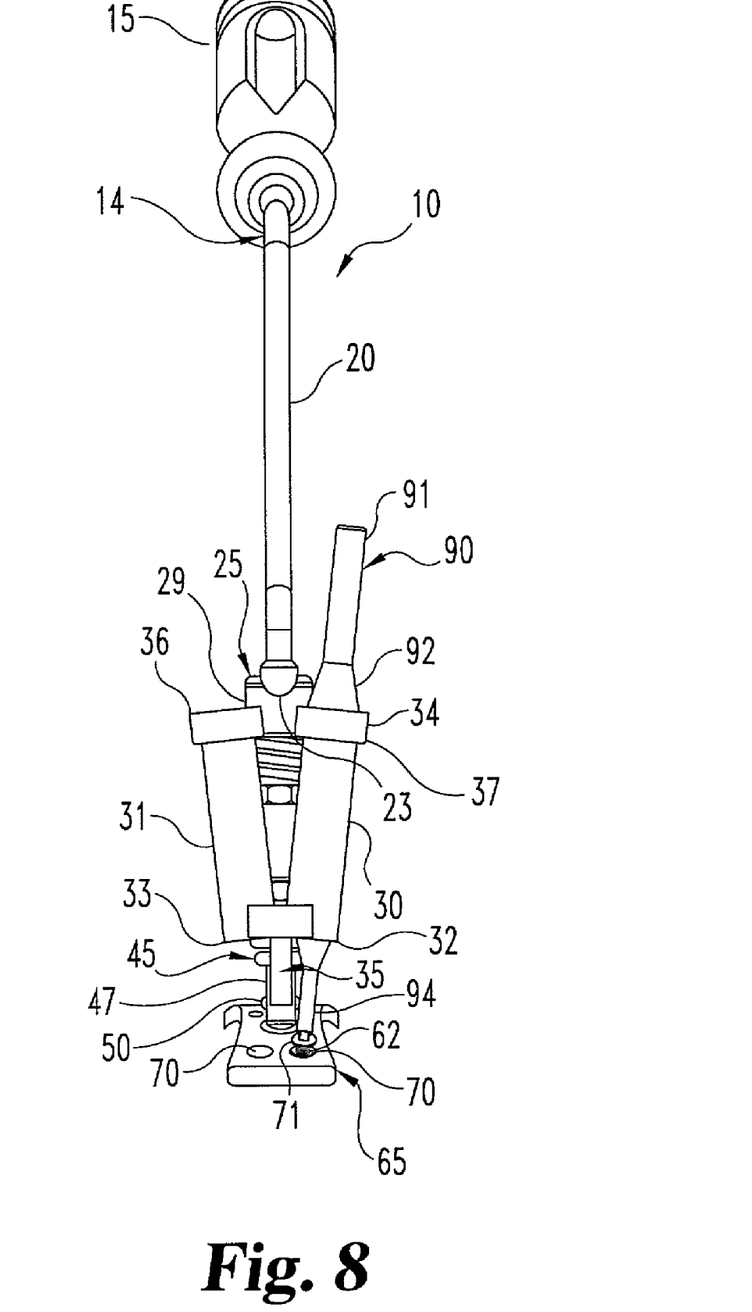
FIG. 8 is a front view of the guide assembly positioned on the bone plate a guide positioned in the guide assembly.

As shown in FIG. 8, a fastener driver 90 is positioned in guide member 30 and has a distal end 94 that engages bone engaging fastener 71 to insert fastener 71 in the respective plate hole 70. Fastener driver 90 can include a main body portion 92 received in form fitting engagement in guide member 30 to guide fastener 70 relative thereto. A proximal end 91 can be engaged by a manual or power tool to rotate driver 90. Fastener 71 can be inserted after drilling a hole into the bony structure underlying plate 65 with, for example, instrument guide 60. If desired, a tapping guide and tap can be inserted through guide member 30 to tap the previously drilled hole. The drilling and, if desired, tapping and fastener insertion could then be repeated through guide member 31 for another plate hole aligned therewith. It is also contemplated that self-tapping fasteners could be employed, and inserted and guided into the drilled hole with guide members 30, 31. It is further contemplated that self-drilling fasteners could be employed and inserted directly into the bony structure using guide members 30, 31 for such placement.

Figure 9:
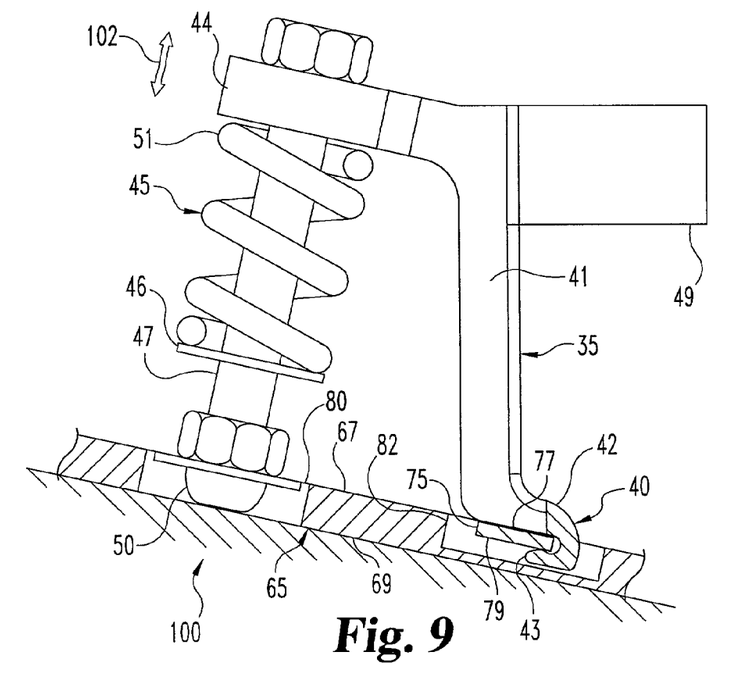
FIG. 9 is a partial cross-sectional view, to a larger scale, of a portion of the bone plate of FIG. 5 with the guide assembly positioned thereon.

Further details regarding the interface of one embodiment guide assembly 10 and bone plate 65 are shown in FIG. 9. FIG. 9 shows a partial cross-sectional view of bone plate 65 along one of the retaining members 75. First member 40 is engageable to retaining member 75 and second member 45 is positioned in alignment with aperture 80. First member 40 is positioned in recess 82 such that lower portion 43 of the foot member slides in a receptacle between distal surface 79 of retaining member 75 and a proximal surface 87 of bone plate 65. Upper portion 42 extends proximally of retaining member 75. Second member 45 is positioned in aperture 80 such that distal end 50 contacts the bony structure 100 underlying plate 65. It is also contemplated that, as shown in FIG. 10, distal end 50 can contact proximal surface 67 of plate 65, or any other proximally facing or generally proximally facing surface of plate 65.

As distal end 50 is positioned in contact with the bony structure, spring member 51 biases support member 41 proximally and thus lower portion 43 into contact with distal surface 79 of retaining member 75. This provides an interference pressure fit between first member 40 and retaining member 75 to secure guide assembly 10 to plate 65. To remove guide assembly 10, the handle can be used to move distal end 50 out of contact with bony structure 100 so that spring member 51 is uncompressed, and first member 40 can slide out from between retaining member 75 and plate 65.

Furthermore, since pin 47 can move relative to support member 41 in the directions indicated by arrow 102, the orientation of guide members 30, 31 relative to the plate holes can be adjusted. Accordingly, second member 45 has a length between extension 44 and its distal end 50 that can vary as spring member 51 is moved between varying states of compression.

Figure 10:
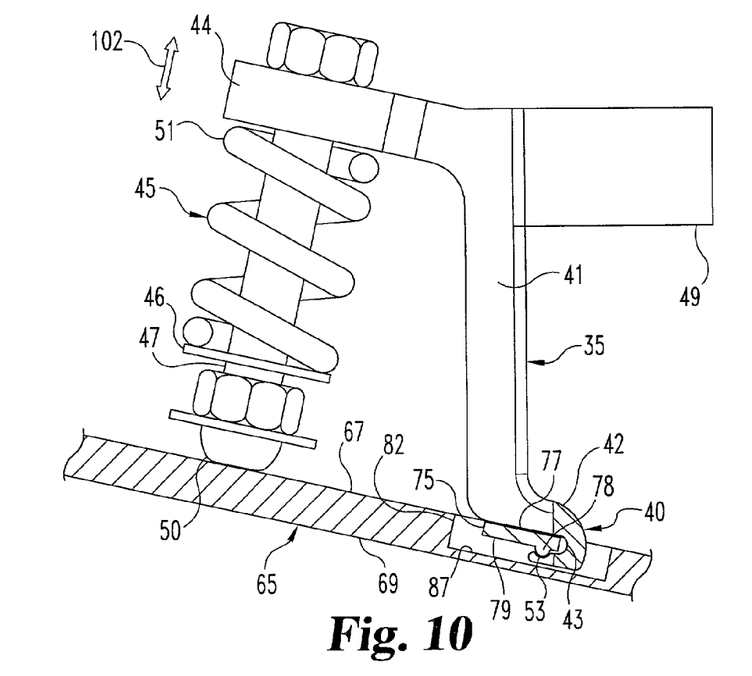
FIG. 10 is a partial cross-sectional view, to a larger scale, of a portion of the bone plate with the guide assembly positioned thereon.

As shown in FIG. 10, in one embodiment retaining member 75 can be provided with a protrusion 78 extending from distal surface 79 thereof. Protrusion 79 can engage a detent (not shown) in plate 65 to prevent retaining member 75 from moving relative thereto when protrusions 84 are engaged to or extend over the bone engaging fasteners in the plate. To accommodate protrusion 78 upon the insertion of lower portion 43 between surfaces 77 and 87, and to allow lower portion 43 to be full inserted in the receptacle therebetween, a notch 53 can be proved in the leading insertion end of lower portion 43. Positioning of protrusion 78 in notch 53 can also prevent retaining member 75 from sliding relative to plate 65 during fastener insertion.

Although plate 65 has been shown with a receptacle that includes retaining member 75 slidably captured therein, other receptacle forms are contemplated. For example, the receptacle could be any opening in the plate that allows lower portion 43 of the foot member to contact a distally oriented surface. Other embodiments contemplate a threaded receptacle or opening suitably configured for engagement with first member 40.

While the invention has been illustrated and described in detail in the drawings and foregoing description, the same is to be considered as illustrative and not restrictive in character. All changes and modifications that come within the spirit of the invention are desired to be protected.

What is claimed is:

1. A guide assembly for a bone plate, comprising:
   at least one guide member alignable with a fastener hole of the bone plate;
   a handle assembly extending proximally from said guide member; and
   a base adapted to support said guide member on the bone plate, said base having a first member engageable with the bone plate and a biasing member contactable with the bone plate to bias said base proximally from the bone plate, wherein said biasing member includes a pin spring-biased for positioning into contact with the bone plate.

2. The guide assembly of claim 1, wherein said at least one guide member includes a guide tube having a passage extending between a proximal end and a distal end thereof.

3. The guide assembly of claim 2, wherein said distal end is spaced a distance from the bone plate when said base is positioned on the bone plate.

4. The guide assembly of claim 2, wherein said guide tube is configured to receive and guide a drill guide instrument therethrough for engagement with the fastener hole in the bone plate.

5. The guide assembly of claim 2, wherein said guide tube is configured to receive and guide a fastener driver therethrough for placement of a bone engaging fastener in the fastener hole of the bone plate.

6. The guide assembly of claim 1, wherein said base includes an extension at a proximal end thereof and said pin extends through said extension, and further comprising a spring contacting said pin.

7. The guide assembly of claim 1, wherein said first member includes a foot member having a hook-shape with a lower portion positionable in a receptacle of the bone plate in contact with a distally oriented surface in the receptacle.

8. The guide assembly of claim 1, wherein said at least one guide member includes two guide members.

9. The guide assembly of claim 8, wherein a first guide member is disposed along a first axis, a second guide member is disposed along a second axis, and said first and second guide members are configured such that said first axis and said second axis converge towards one another distally.

10. The guide assembly of claim 9, wherein said first guide member and said second guide member are configured such that said first axis and said second axis converge at an angle of about 12°.

11. A guide assembly for a bone plate, comprising:
    at least one guide member;
    a handle assembly extending proximally from said at least one guide member; and
    a base positionable relative to the bone plate to support said at least one guide member in alignment with a fastener hole of the bone plate, said base including a first member contactable with a distal surface of the bone plate and a second member contactable with one of a proximal surface of the bone plate and bony structure underlying the bone plate to secure said at least one guide member in alignment with the fastener hole of the bone plate, wherein
    said base includes a support member extending distally from said at least one guide member and said first member includes a foot member extending laterally from said support member; and
    the second member includes a pin extending distally from a proximal end of said support member, wherein said pin is spring-biased into contact with one of the proximal surface of the bone plate and bony structure underlying the bone plate.

12. The guide assembly of claim 11, wherein said foot includes an upper portion and a lower portion defining a space therebetween to receive a portion of the bone plate therein.

13. The guide assembly of claim 11, wherein said at least one guide member includes a guide tube having a passage therethrough extending between a proximal end and a distal end thereof.

14. The guide assembly of claim 13, wherein said distal end is spaced a distance from the bone plate when said guide member is secured in alignment with the fastener hole of the bone plate.

15. The guide assembly of claim 14, wherein said guide tube is configured to receive and guide a drill guide tube therethrough for engagement with the fastener hole of the bone plate.

16. The guide assembly of claim 14, wherein said guide tube is configured to receive and guide a fastener driver therethrough for engagement of a fastener in the fastener hole of the bone plate.

17. A surgical drill guide assembly for a bone plate having at least one hole for a fastener comprising:
    at least one guide member alignable with a fastener hole of the bone plate;
    a handle assembly extending from said at least one guide member;
    means for supporting said at least one guide member relative to the bone plate with said at least one guide member aligned with the at least one hole, wherein said means for supporting includes means for biasing said means for supporting proximally relative to the bone plate.

18. The guide assembly of claim 17, wherein said means for supporting includes a support member having a proximal end and a distal end, said at least one guide member being coupled to said support member.

19. The guide assembly of claim 18, wherein said support member includes a hook-shaped foot extending laterally from said distal end thereof and a pin distally biased from said proximal end of said support member toward the bone plate, wherein when said pin contacts said bone plate said means for supporting is biased proximally into contact with a distal of surface of the bone plate.

20. The guide assembly of claim 17, wherein said at least one guide member includes two guide members.

* * * * *